United States Patent [19]

Beckmann

[11] 4,214,701
[45] Jul. 29, 1980

[54] IRRIGATION VALVE DEVICE

[76] Inventor: Gerhard Beckmann, Tödiweg 51, 7988 Wangen, Allgäu, Fed. Rep. of Germany

[21] Appl. No.: 937,600

[22] Filed: Aug. 28, 1978

[30] Foreign Application Priority Data

Sep. 2, 1977 [DE] Fed. Rep. of Germany ....... 2739650
Dec. 6, 1977 [DE] Fed. Rep. of Germany ....... 2754307
Aug. 10, 1978 [DE] Fed. Rep. of Germany ....... 2835093

[51] Int. Cl.² .......................................... H01G 27/00
[52] U.S. Cl. ........................................ 239/63; 405/37
[58] Field of Search ................. 237/63, 11, 49; 47/79, 47/80, 81, 82, 48.5; 73/73, 337; 137/78; 236/44 A; 405/37

[56] References Cited

U.S. PATENT DOCUMENTS

3,426,539 2/1969 Whear ..................................... 405/37

*Primary Examiner*—James B. Marbert
*Attorney, Agent, or Firm*—Oblon, Fisher, Spivak, McClelland & Maier

[57] ABSTRACT

An irrigation valve device including a swellable member and a support therefor permitting moisture to reach the swellable member. Part of the support can be buried in the ground to an adjustable extent to vary the amount of moisture reaching the swellable member. The swellable member acts on irrigating water supply means to control the amount of irrigation water in response to the degree of swelling.

31 Claims, 8 Drawing Figures

IRRIGATION VALVE DEVICE

BACKGROUND OF THE INVENTION

1. Field of the Invention

The invention relates to an irrigation valve device comprising a valve and a swellable member which controls the valve in response to its moisture content and is subjected to the water passing through the valve.

2. Description of the Prior Art

A known irrigation valve of this kind comprises a swellable member consisting of wood chips which are accommodated in an apertured cylinder and act on a magnetic valve. The magnetic valve is included in an irrigation conduit which feeds a lawn sprinkler. The latter is arranged so that the water sprayed from it reaches the horizontally disposed apertured cylinder and, through the apertures in the cylinder, the swellable member. When sufficient water has been absorbed, the swellable member closes the magnetic valve. For the purpose of regulating the flow of water to the swellable member, the periphery of the apertured cylinder has apertures which differ in number and diameter. By turning the apertured cylinder, a different total cross-sectional area is offered to the sprayed water so that the latter will contain more or less water at a given spraying intensity. One disadvantage of this irrigation valve resides in the fact that the apertured cylinder to a very large extent covers the swellable member from the outside and consequently the surrounding air does not have adequate access to the swellable member for the purpose of drying the same. As a result, there is a very long drying period during which no spraying can take place. In addition, the magnetic valve is either open or closed and thus in the open position of the magnetic valve an excessive supply of water must be offered to the plants so that the latter can withstand the period during which the magnetic valve is switched off. However, artificial irrigation is more rational and more effective if the water can be supplied with more continuity.

German Gebrauchsmuster No. 77 06 643 describes another irrigation valve device that works with a swellable member of wood which is accommodated in an apertured cylinder, has one end acting on a diaphragm valve and its other end supported against a screw-threaded plug. By screwing the plug into the apertured cylinder to a greater or lesser extent one can adjust the response threshold of this known hygrostat. Since this irrigation valve device is intended to be buried in the earth, adjustment of the response threshold of the valve by turning the plug is very cumbersome to start with because, since the plug is located at the lower end of the valve, it must be dug out of the earth completely. Further, adjustment of the play for the swellable member is basically inadequate to achieve optimum artificial irrigation because only the length of swelling is set at which the valve will close or open but one cannot, for example, vary the frequency of operation. Apart from the poor accessability of the plug for setting the response threshold, the installation of the hygrostat in the earth has the additional disadvantage that the swellable member cannot be dried out by the outside air. However, the dissipation of moisture by the wood to the earth is too slow for the irrigation of plants because, in contrast with a plant, the swellable member does not withdraw water from the earth and hence the earth in the vicinity of the wooden member remains moist for a longer period than in the region of a plant using up water. These long inoperative periods have to be compensated by correspondingly intensive irrigation of the plants during the operative periods of the valve, which is contrary to the aim of achieving a water supply that is as continuous as possible.

DE-AS No. 1 191 163 describes an apparatus in which the swelling of a swellable member in the form of a wooden rod pinches a water hose and thereby inhibits the supply of water to a plant container, the swellable member being subjected to liquid from the earth by way of a sponge in the base of the plant container. In this apparatus there is likewise a set screw for the play of the swellable member, with which one can merely set the degree of swelling of the swellable member at which the hose will be pinched shut.

DE-AS No. 1 039 296 describes an automatic irrigating apparatus for cultivated plants, in which a hygrometer at the end of a tube insertable in the earth controls a liquid valve disposed at the other end of the tube. The humidity threshold at which the valve is to be actuated can for example be regulated by a set screw. Again, this irrigating apparatus has inherent disadvantages resulting from the accommodation of the hygrometer in the earth.

A humidity-controlled valve of quite a different kind is disclosed in DE-OS No. 2 513 600. This known valve adapts the irrigation to atmospheric conditions, i.e. the valve remains closed during rain or very humid conditions and opens for a predetermined adjustable time interval when it is dry. The irrigating water passing through the valve is not returned to the swellable member.

A control device described in DE-OS No. 23 25 980 comprises a valve member in which the interior accommodates a swellable member acting on the valve seat and which has lateral apertures and a top aperture for the entry of water for swelling purposes. The valve member is placed on or in the earth. There is no provision for setting a particular control behavior of the device.

Finally, U.S. Pat. No. 3,512,712 describes an automatic irrigating apparatus that operates with a humidity sensor which is connected by way of a wick to the part of the earth to be watered and is otherwise subjected to the humidity of the air. The humidity film comprises a swellable member in the form of hollow cylindrical blocks of which the swelling is transmitted to an indicating apparatus and to an irrigating valve. The supply of water for swelling purposes from the earth to the swellable member cannot be controlled.

SUMMARY OF THE INVENTION

The invention has the object of providing an irrigation valve device of the aforementioned kind that is adjustable to an optimum.

This object is achieved according to the invention in that the irrigation valve device is constructed to be insertable in the earth so that the swellable member or a water-permeable receptacle therefor makes contact with the earth over an adjustable distance to control the supply of swelling water to the swellable member.

By means of the construction of the irrigation valve device according to the invention, the swellable member or the receptacle therefor is sub-divided into an upper and a lower section, the lower section being wetted by the swelling water which reaches the valve device through the earth and the upper section, which is subjected to weather influences, is moistened as a result of capillary action. This achieves excellent adjustability of the irrigation. In so far that the size of the wetted lower section of the swellable member or the receptacle therefor and the unwetted upper section are varied, a change is produced in the time taken to achieve a predetermined degree of swelling. The time becomes all the longer, the less deeply the swellable member or the receptacle penetrates into the earth and it is shortened by deeper insertion of the swellable member or receptacle into the earth. In this way one can set the irrigation to be very close to ideal conditions.

If, in accordance with an advantageous development of the invention, wood is used for the swellable member, one exploits the fact that the swelling of wood is considerably faster with direct wetting of watering than it is when moisture is absorbed under capillary action. The time taken until a degree of swelling is achieved at which the valve closes is practically the sum of the change in length periods of the lower section of the swellable member that is wetted directly and the upper section that is moistened by capillary action. Another possibility of influencing the swelling time, namely that proportion of the time accounted for by the capillary moistening of the wooden swellable member, is by arranging the wooden swellable member at an angle to the vertical. It has been found that swelling of an elongate wooden swellable member is all the more rapid when receiving water under capillary action the more the elongate member is inclined from the vertical. In addition, the swellable length that can be wetted by receiving water under capillary action in the first place becomes all the longer, the more the wooden swellable member is inclined from the vertical.

According to one particular construction of the invention, the swellable member is of swellable plastics material, particularly polyurethane gel. Polyurethane gel has an extraordinarily large swellability so that even very small swellable members can bring about large valve-actuating distances and forces.

Desirably, the swellable member of swellable plastics material is accommodated in a perforated sleeve serving as the valve member and acts on a pinchable hose which is passed through the sleeve. By inserting the sleeve in the earth to a greater or smaller extent, one then obtains an effect of adjustment that is similar to that with a wooden swellable member.

Since the swelling times up to closure of the valve and shrinkage periods up to opening thereof are all the shorter as the swellable member is smaller and product short swelling and shrinkage periods so that the plants to be irrigated are supplied with water in a multitude of small quantities, the invention also suggests an irrigation valve device comprising a very small swellable member of swellable plastics material. More particularly, an elongate member of porous material, particularly ceramic, serving as the receptacle has in its upper end face a recess in which the swellable member of swellable plastic material, especially polyurethane gel, is accomodated and this, in turn, has its upper face abutting an elastic sealing element of the valve that is seated on the top of the receptacle. This sealing element of the valve acts as a valve actuating element and, upon swelling of the swellable member, is pushed upwardly in the direction of closing the valve. The swellable member is thus enclosed by the receptable and the sealing element so that water for swelling purposes can reach the swellable member solely by way of the porous material of the receptacle. The direct supply of water to the swellable member as is possible in the case of a swellable member accommodated in a perforated sleeve is thus suppressed. By inserting the receptacle in the earth to a larger or smaller extent, its proportion of length directly subjected to the moisture of the earth is varied, whereby one can also control the supply of swelling water to the swellable body as a result of capillary action in the porous receptacle. The swellable member thus swells only as a result of water conveyed under capillary action. The section of the receptacle projecting from the earth is subjected to weather influences, i.e. the effects of the sun and wind, and extracts the moisture that was absorbed by the swellable member. The swellable member can be comparatively small because it need not extend to the part of the receptacle that is seated in the earth, thereby resulting in desirably short swelling and shrinkage periods.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views, and wherein.

DETAILED DESCRIPTION OF THE PREFERRED EMBODIMENTS

Figure 1:
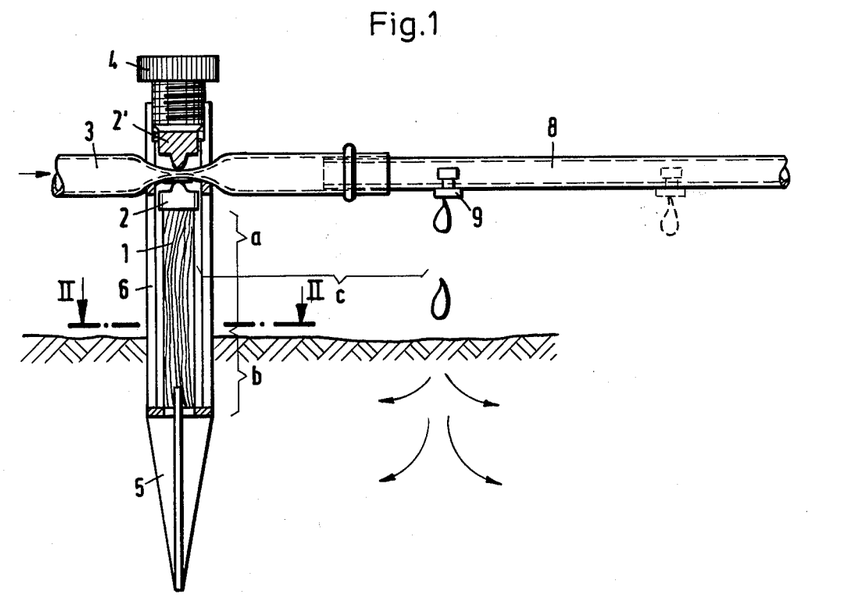
FIG. 1 illustrates a first example of an irrigation valve device employing a wooden swellable member.
Figure 2:
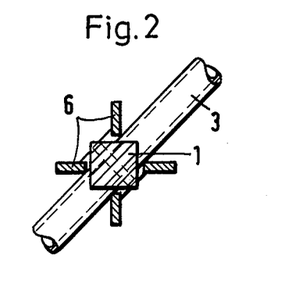
FIG. 2 is a section on the line II—II in FIG. 1.

The irrigation valve device of FIG. 1 serves to irrigate more extensive areas. The swellable member 1 which, as is shown in FIG. 2, is of square cross-section and can for example be of spruce, fir or pine, the length of the swellable member 1 being tangential to the annual rings, acts on a pinchable hose 3 by way of a pinching beam 2 which is guided against tilting. The swellable member 1 is accommodated in a valve member 5 in the form of a peg insertable in the earth and is guided by four guide ribs 6 (FIG. 2) and secured against buckling. The valve member 5 has an insert opening at its upper end for the swellable member 1 and is closed by a set screw 4. The pinchable hose 3 passes through the valve member between the guide ribs 6 and rests on the pinching beam 2. A second pinching beam 2' is provided between the pinchable hose 3 and the set screw 4. The pinchable hose 3 communicates with a water supply on the left-hand side of FIG. 1 and feeds an irrigation hose 8 which lies on the ground and extends to the plants to be watered. Drip nipples 9 are provided on the irrigation hose 8 at desired intervals but these can be replaced by perforated drip hoses.

The swellable member 1 is first saturated with water for 24 hours and then inserted in the valve member 5. The set screw 4 is then tightened just sufficiently so that water no longer flows through the pinchable hose 3. This ensures that, every time the wooden swellable member 1 shrinks, water will pass through the valve. The irrigation valve device is then inserted in the earth, as shown in FIG. 1. The lower section b of the swellable member 1 enters the earth while the upper section a remains exposed. The first drip nipple 9 is spaced from the swellable member by the distance c.

Water dripping from the drip nipple 9 when the valve is open enters the earth and, under capillary action, traverses the distance c to reach the swellable member 1. By displacing the pinch hose 3 in the valve, this spacing c of the drip nipple can be altered. The water reaching the swellable member 1 wets same directly along the section b whereas absorption at the section a is under capillary action. Since the swelling period for the section a is relatively long and for the section b relatively short, one can set the desired duration of irrigation by inserting the irrigation valve device to a greater or less extent. When the swellable member is inserted deeply, this period is short and when it is inserted to a shallower extent it is long.

The length of the swellable member must be adapted to the diameter of the pinch hose. To achieve a large throughflow quantity, the pinch hose 3 must have a large diameter and the swellable member 1, which has a square cross-section with sides of about 10 mm, must be correspondingly long so that an adequately long shrinkage distance is available to open the valve. Apart from the adjustability of the irrigating time by inserting the irrigation valve device in the earth to a greater or lesser extent, further adjustment can be obtained by inclining the valve member 5 and thus the swellable member 1 to the vertical, which is not particularly illustrated in the drawing but which will be readily understood from the foregoing explanations about the absorption of water under capillary action.

The pinch hose 3 is desirably of inert silicon or neoprene. The irrigating hose 8 connected to the pinch hose 3 is of polyethylene. The valve member itself can be of inert metal or plastics material.

Figures 3, 4:
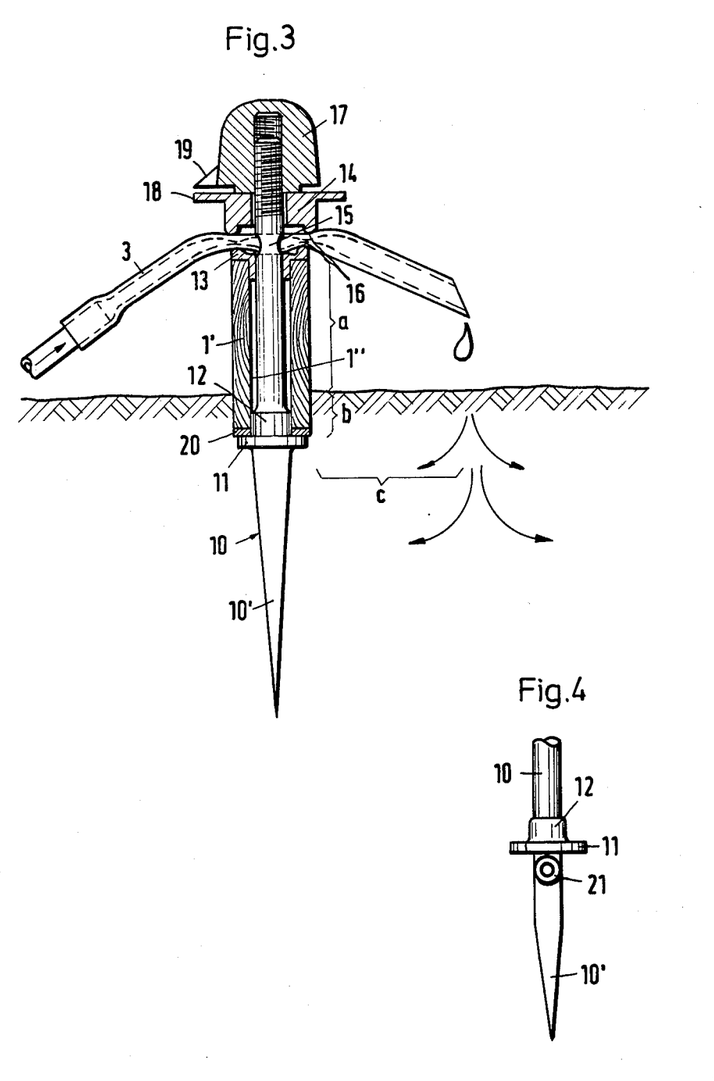
FIG. 3 shows a second example of an irrigation valve device employing a wooden swellable member.
FIG. 4 illustrates an insertion tip for the FIG. 3 example provided with a hinge.

Whereas the irrigation valve device of FIG. 1 is suitable for a plurality of drip outlets and a correspondingly high water pressure, the irrigation valve device of FIG. 3 is also suitable for a low water pressure (e.g. for household gardens or from a rain-collecting drum). More particularly, the device of FIG. 3 is provided with a single drip outlet. The swellable member 1' contains a bore 1" and is placed over the valve member 10. Above the lower insertion tip 10', the valve member 10 has a flange 11 on which the swellable member 1' is supported and a superposed extension 12 which centres the swellable member 1' at the bottom. At its upper end, the swellable member 1' is centred by a valve portion 13 which slides on the valve member 10 and between which and a superposed valve portion 14 the pinch hose 3 extends through a hole or slot 15 in the valve member 10. The valve portions 14 and 15 each have a pinch bead 16, the pinch hose 3 being squeezed between the pinch beads 16. The lower pinch bead has a smaller diameter than the upper bead so that the pinch hose 3 inclines downwardly in an arc. The drip outlet is thus at a fixed position and drops cannot run along the pinch hose 3, which could easily happen if the pinch hose 3 were to be horizontal. The position of the upper valve portion 14 is secured by a cap 17 screwed to the top of the valve member 10. The top of the valve portion 14 has a graduated scale 18 whereas the cap comprises a corresponding pointer 19. The upper valve portion 14 is then desirably guided on the valve member 10 for only longitudinal displacement but not rotation. Beneath the swellable member 1' there can be positioned a fault washer 20. With regard to setting the irrigating period, the same applies here as was described in relation to FIG. 1. This means that the spacing c can be changed by displacing the pinch hose 3 and the sections a and b can be varied by inserting the swellable member in the earth to a greater or lesser extent. Again, inclining the valve member is an additional means of adjustment.

FIG. 4 shows a different insert tip 10' for the valve member of FIG. 3. The FIG. 4 valve member 10 comprises a hinge 21 for tilting the swellable member 1' sideways.

Whereas in the previously described examples the swellable member is made from wood, preferably spruce, fir or pine exploiting the swelling effect tangentially to the annular rings, the swellable members of the following examples employ swellable plastics material which is elastic, particularly expansible. On the one hand, this material exhibits greater swellability than does wood. On the other hand, it has an advantage over wood in that, if the swellable member is suitably encapsulated, the elasticity of the plastics material makes it possible to increase its change in length by inhibiting expansion in the other directions. In this way one can, despite relatively short swellable members, achieve an adequately long swelling stroke to actuate the valve. A particularly high degree of swellability is exhibited by polyurethane gel which is very easy to process.

Figure 5:
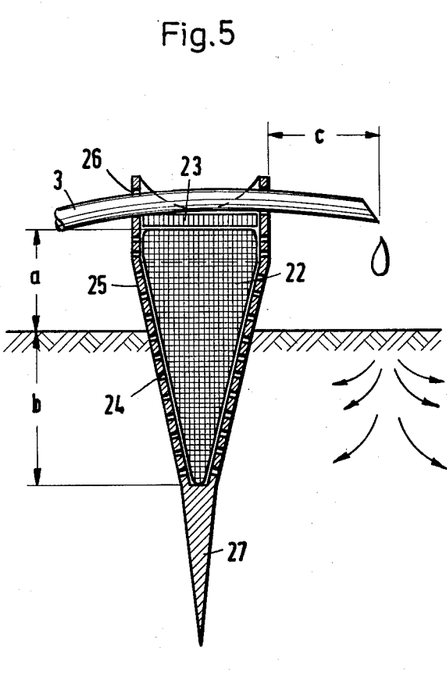
FIG. 5 is a cross-section through a first example of irrigation valve device with a swellable member of swellable plastics material.
Figure 6:
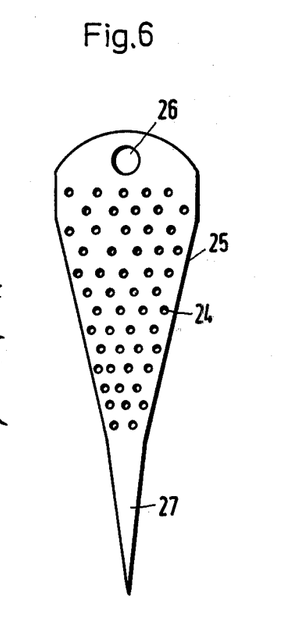
FIG. 6 is a side elevation of the irrigation valve device according to FIG. 5.

The irrigation valve device shown in FIG. 5 comprises a swellable member 22 of polyurethane gel acting on a pinch hose 3 by way of a pinch plate 23. Th pinch hose is seated in a sleeve 25 which has perforations 24, receives the swellable member 22 serving as the valve member and is provided at its upper edge with two opposed apertures 26 through which the pinch hose 3 is passed. By means of an insert tip 27 formed at the lower end of the sleeve 25, the sleeve is inserted in the earth such that a section b of the swellable member extends into the ground.

The swellable member 22 has a conical or pyramidal shape corresponding to that of the sleeve 25. Apart from polyurethane gel for the swellable member 22, of course all elastic plastics materials are suitable which have a sufficient swelling behavior. In addition, the shape of the swellable member is not restricted to that illustrated. A rod-shaped swellable member can for example be provided of which the cross-section is circular, square or polygonal. What is important is only that the swellable member 22 acts on the pinch hose in such a way that it shuts the pinch hose 3 before or whilst it reaches its maximum swelled condition.

The pinch plate 23 only serves to transmit to the pinch hose 3 the upwardly directed force exerted by the swellable member 22 and it desirably consists of a plastics material which is somewhat less elastic than the material of the swellable member.

The sleeve 25 is desirably of plastics material and has a wall thickness ensuring that the sleeve is not markedly deformed under the swelling action of the swellable member 22. The sleeve 5 may also be of metal or ceramic material. Its wall which is in contact with the swellable member 22 is provided with perforations 24 in the form of a multitude of small holes enabling the penetration of the water.

This irrigation valve device may be provided upstream of a single drip outlet as is shown in FIG. 5 or used to feed an irrigation hose having a plurality of drip outlets, for example in the form of drip nipples. These are two possiblities for setting the amount of water passing through the valve device. First, the irrigation valve devices can be inserted in the earth to a greater or less extent, thereby varying the sections a and b of the swellable member 22. The other possibility for adjusting the quantity is varying the spacing of the first drip outlet downstream of the irrigation valve device from the valve device by, for example, displacing the hose 3 to the right or left in FIG. 5. In this way one changes the spacing c.

Further, the control behavior of the irrigation valve device is determined by the swelling behavior of the swellable member and the space available inside the sleeve 25. With given dimensions for the sleeve 25, the size of the swellable member 22 is desirably selected so that the pinch hose 3 is just squeezed shut when the swellable member 22 has expanded to a maximum. This means that even the slightest amount of shrinkage of the swellable member subsequent to the pinch hose being squeezed shut will immediately open the pinch hose again, whereby the closure times can be kept relatively short and the irrigating water can be fed to the plants in a multitude of small quantities. The irrigation valve can thus be placed in a position of equilibrium in which it delivers just enough water as it requires to maintain this condition.

However, it is also possible to make the apertures 26 at the top of the sleeve 25 in the form of slots and to provide an upper counterbearing for the pinch hose 3 in the form of a longitudinally displaceable pinch beam which is mounted in the sleeve 25 and the position of which can be adjusted by a set screw engaging in the upper end of the sleeve 25. With the aid of such an adjusting screw one can then set the swelling condition of the swellable member in situ to one where the pinch hose is squeezed shut as in the case of the FIGS. 1 and 3 examples.

Figures 7, 8:
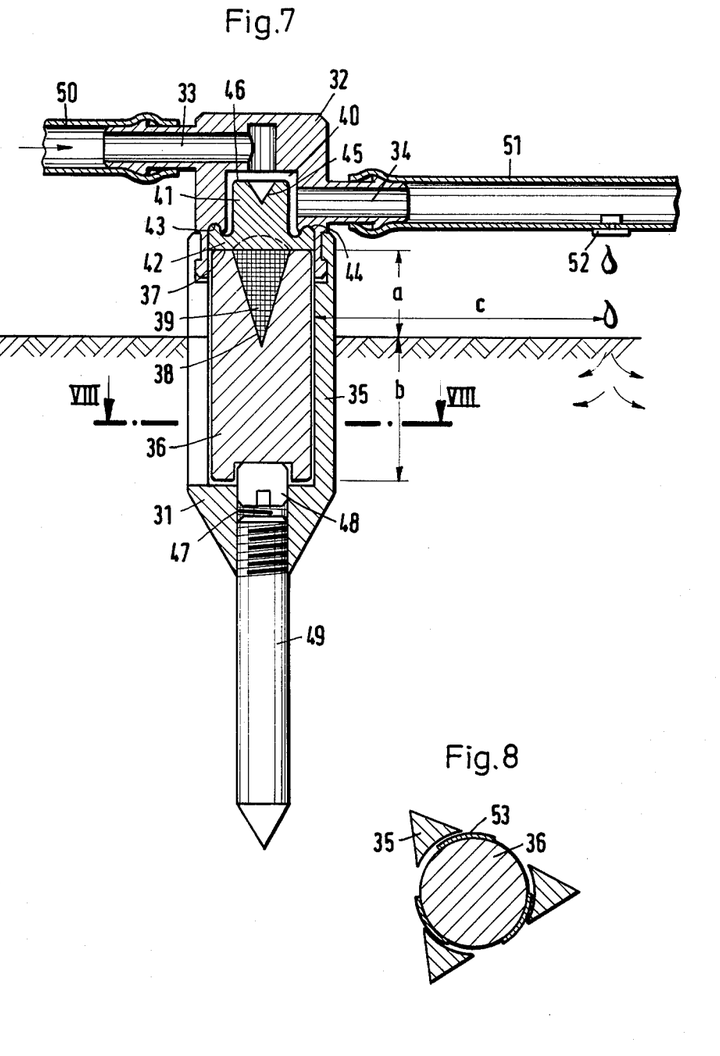
FIG. 7 is a cross-section of a second example of irrigation valve device with a swellable member of swellable plastics material accommodated in a ceramic receptacle.
FIG. 8 is a cross-section of the FIG. 7 device on the line VIII—VIII.

The irrigation valve device of FIGS. 7 and 8 comprises a housing 31 on the upper end of which there is placed a valve member 32 having an inlet 33 and an outlet 34. The inlet and outlet are in the form of hose connectors. The housing 31 has three longitudinal ribs 35 embracing a receptacle or receiving member of porous material in the form of an elongate ceramic cylinder 36 in the upper end face 37 of which there is located a conical recess 38 receiving a likewise conical swellable member 39 of polyurethane gel.

The interior of the valve member 32 forms a cylindrical valve chamber 40 of which the longitudinal axis extends in the longitudinal direction of the irrigation valve device. The supply 33 opens axially into the upper end face of the valve chamber 40 whereas the outlet 34 opens into the wall of the cylindrical valve chamber 40. An elastic sealing element in the form of a rubber cylinder 41 enters the valve chamber 40 from below and at its lower end it is formed with a flange 42. The flange 42 has its lower face lying on the upper end faces of the ceramic cylinder 36 and swellable member 39. The upper face of the flange 42 forms an annular bead 43 which penetrates into an annular groove 44 of the valve member 32. The upper face of the cylinder 41 is formed as a valve plate surface 46 with the aid of a conical recess 45, the plate surface closing the supply 33 when the swellable member 39 is it its swollen condition (shown in broken lines in FIG. 7) and lifts the cylinder 41. The diameter of the cylinder 41 is smaller than the diameter of the cylindrical valve chamber 40 to an extent such that the swellable member can continue to swell even after the valve has been closed and this swelling is absorbed by the cylinder 41 becoming spherical.

The housing 31, of which the longitudinal ribs 35 are positively connected to the valve member 32, has at its lower end a central longitudinal tapped hole 47 in which a grub screw 48 is inserted from below. With the aid of the grub screw 48 the ceramic cylinder 36 is pressed upwardly so that the flange 42 is tightly clamped between the ceramic cylinder 36 and the valve member 32. In addition, the position of the cylinder 41 is set in the unswollen condition of the swellable member 39, the elasticity of the flange 42 being utilized. Beneath the grub screw 48 an insert tip 49 is screwed into the tapped hole 47.

Water holes 50 and 51 are pushed over the connectors of the inlet 33 and outlet 34. The hose 50 serves to connect the irrigation valve device to a water supply. If this water supply delivers an excessively large pressure, it is desirable to include a reducing valve between the water supply and the irrigation valve device. The hose 51 connected to the outlet 34 is provided with a series of drip nipples of which the first nipple 52 is illustrated in FIG. 1 and has a spacing c from the ceramic cylinder 36. A hose 51 having up to 50 drip outlets can, for example, be employed. The valve is first set in the unswollen condition of the swellable member 39 in that the grub screw 48 is tightened until the valve plate 46 just closes the supply 33. The grub screw is then turned back to a certain degree, for example half a turn, which sets the degree of swelling of the swellable member 39 at which the valve will close. The irrigation valve device is thereupon inserted in the earth as shown in FIG. 7. The water leaving the drip nipple 52 enters the earth, part of this water reaching the ceramic cylinder 36 as swellable water after it has traversed the distance c in the earth. This swelling water wets the lower section b of the ceramic cylinder 36 that is in contact with the earth and enters same. Under capillary action, the penetrated swelling water then moves upwardly into the exposed section a of the ceramic cylinder 36 and reaches the swellable member 39 to moisten the same. Subsequent swelling of the swellable member causes the cylinder 41 to be lifted until the valve plate 46 closes the supply 33. The upper section of the ceramic cylinder 36 having the length a is subjected to wind and sun so that the penetrated swelling water evaporates in response to the weather conditions, which eventually causes the valve to open again and result in renewed irrigation of the earth. To set this cycle so that the plants to be irrigated receive just the required amount of water, the irrigation valve device is inserted in the earth to a greater or less extent. An alteration in the supply of water to the swellable member can also be achieved by changing the spacing c of the drip nipple 52.

A further possibility of adjustment for the irrigation cycle is made available in that the wall of the ceramic cylinder 36 is provided with glazing strips 53 which extend lengthwise of the cylinder and which are angularly spaced by 120° as are the longitudinal ribs 35. The ceramic cylinder 36 cannot receive or dissipate moisture at the position of these glazing strips 53. The width of the glazing strips 53 is substantially the same as that of the longitudinal ribs 35 in the region of which moisture can likewise not be absorbed or dissipated. If, therefore, the ceramic cylinder is turned so that the glazing strips 53 are disposed entirely beneath the longitudinal ribs 35, the surface of the ceramic cylinder 36 exposed for the reception and delivery of moisture is at a maximum. The more the glazing strips 53 are turned out from the vicinity of the longitudinal ribs 35, the smaller will be the surface of the ceramic cylinders 36 that is available for receiving and delivering moisture. FIG. 8 illustrates the case where the exposed ceramic surface of the ceramic cylinder 36 is reduced by about 50%.

If only a single plant is to be irrigated with the irrigation valve device as described, a short hose at the outlet 34 of the valve will be sufficient if it has a length equal to the desired spacing c.

On the other hand, if the irrigation valve device is to irrigate a large area, it can be used as control valve means for a larger hydraulically controllable valve. The valve 51 will then not have a drip nipple 52 and terminate at a spacing c from the irrigation valve device. The hose 50 is connected to the control input of the hydraulically controllable valve, of which the throughput capacity is correspondingly larger. As soon as the valve as described opens, the water pressure in the hose 50 is reduced and this is sufficient to open the valve to be controlled. The water reaching the earth from the end of the hose 51 penetrates up to the swellable member 39 until the latter closes the valve, whereby the pressure in the hose 50 is built up again and the valve to be controlled is closed again. The latter therefore operates in synchronism with the valve controlled by the swellable member. Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An irrigation valve device comprising:
a valve;
a swellable member operatively associated with the valve which controls the valve is response to its moisture content and is subjected to water passing through the valve, said valve further comprising:
an insert tip extending below said swellable member for insertion into ground, at least a major portion of the surface of said swellable member being exposed above ground and the remaining portion of the surface of said swellable member directly contacting the ground in accordance with depth of insertion of the inert tip into the ground.

2. An irrigation valve device as set forth in claim 1, wherein said valve includes an outlet conduit which terminates at an adjustable distance from the swellable member.

3. An irrigation valve device as set forth in claim 1, wherein said valve includes an outlet conduit which is provided with drip outlet means at an adjustable distance from the swellable member.

4. An irrigation valve device as set forth in claim 1, said valve including a counterbearing and further comprising a pinch hose mounted with said valve and engageable with said pinch hose.

5. An irrigation valve device as set forth in claim 4, said valve member comprising:
a peg member;
rib members for guiding said swellable members; and
a head member in the form of a screw-threaded socket member and set screw for receiving said swellable member and the pinch hose.

6. An irrigation valve device as set forth in claim 1, wherein said swellable member comprises wood.

7. An irrigation valve device as set forth in claim 1, wherein said valve member comprises plastic material.

8. An irrigation valve device as set forth in claim 7, wherein said plastic material comprises polypropylene.

9. An irrigation valve device as set forth in claim 4, said swellable member having a transverse recess and a longitudinal hole formed therein, said valve being partially positioned in said longitudinal hole and said pinch hose being received by said transverse recess and further comprising a bush member adjustably seated on the valve member.

10. An irrigation valve device as set forth in claim 9, further comprising hinge means for tiltably connecting said valve member with said insert tip.

11. An irrigation valve device comprising:
a valve including a perforated sleeve in the form of an acute cone;
a swellable member operatively positioned within the valve which controls the valve in response to its moisture content and is subjected to water passing through the valve, said swellable member comprising polyurethane gel wherein at least one portion of the surface of said swellable member is exposed above ground and the remaining portion of the surface of said swellable member directly contacts the ground in accordance with depth of insertion of the valve into the ground.

12. An irrigation valve device as set forth in claim 11, wherein said valve includes an outlet conduit which terminates at an adjustable distance from the swellable member.

13. An irrigation valve device as set forth in claim 11, further comprising a pinch hose, said acute cone including opposed apertures for receiving the pinch hose and a pinch plate mounted within the acute cone and disposed between said swellable member and the pinch hose.

14. An irrigation valve device as set forth in claim 11, wherein said valve comprises a plastic material.

15. An irrigation valve device as set forth in claim 14, wherein said plastic material of said valve comprises polypropylene.

16. An irrigation valve device comprising:
a valve;
a swellable member operatively associated with the valve which controls the valve in response to its moisture content and is subjected to water passing through the valve, said swellable member comprising:
an elongated porous receiving member with a recess formed in an upper end face portion of said receiving member; and
a swellable insert member positioned in said recess formed in said receiving member wherein said swellable insert comprises polyurethane gel and at least one portion of the surface of said swellable member is exposed above ground and the remaining portion of the surface of said swellable member contacts the ground in accordance with depth of insertion of the valve into the ground.

17. An irrigation valve device as set forth in claim 16, wherein said valve includes an outlet conduit which terminates at an adjustable distance from the swellable member.

18. An irrigation valve device as set forth in claim 16, wherein said valve includes an outlet conduit which is provided with drip outlet means at an adjustable distance from the swellable member.

19. An irrigation valve device as set forth in claim 16, said valve further comprising an elastic sealing element seated on said receiving member, the upper face of the swellable insert abutting against said elastic sealing element.

20. An irrigation valve device as set forth in claim 16, wherein said receiving member comprises a ceramic cylinder.

21. An irrigation valve device as set forth in claim 16, wherein said recess formed in said receiving member and said insert member are conically shaped.

22. An irrigation valve device as set forth in claim 20, further comprising a housing member insertable into the ground having a plurality of longitudinal ribs for holding said ceramic cylinder, said valve being connected to said housing member at an upper end portion of the housing member.

23. An irrigation valve device as set forth in claim 19, said valve defining a valve member having an inlet and an outlet wherein said elastic sealing element sealingly projects into the chamber so as to open or close the inlet under the influence of the swellable member.

24. An irrigation valve device as set forth in claim 23, said valve including an annular face and said elastic sealing element being in the shape of a cylinder and further comprising a valve plate member formed at the upper end face thereof facing said inlet and a flange member abutting upper end faces of the ceramic cylinder and the swellable member and including an upwardly directed flange face in sealing engagement with said annular face of the valve.

25. An irrigation valve device as set forth in claim 24, said annular face of said valve including an annular groove formed therein and said flange member includes an annular bead portion engaged within said annular groove formed in said annular face.

26. An irrigation valve device as set forth in claim 23, wherein the volume of said valve chamber is such as to accommodate further swelling of the swellable member after the valve has been closed due to elastic deformation of said elastic sealing element (41).

27. An irrigation valve device as set forth in claim 22, said housing including a screw-threaded hole formed therein and further comprising an adjustable screw seated in said screw-threaded hole engageable with a lower end portion of the ceramic cylinder along the longitudinal axis of the ceramic cylinder.

28. An irrigation valve device as set forth in claim 27, said adjusting screw comprising a grub screw and said housing including a tapped hole formed therein below said grub screw and further comprising an insert tip member fixed within said tapped hole.

29. An irrigation valve device as set forth in claim 22, wherein said valve and said housing comprise plastic material.

30. An irrigation valve device as set forth in claim 29, wherein said plastic material comprises polypropylene.

31. An irrigation valve device as set forth in claim 19, wherein said sealing element comprises rubber.

* * * * *